US011141565B2

(12) United States Patent
Coker et al.

(10) Patent No.: US 11,141,565 B2
(45) Date of Patent: Oct. 12, 2021

(54) ECHOGENIC COIL MEMBER FOR A CATHETER ASSEMBLY

(71) Applicant: Avent, Inc., Alpharetta, GA (US)

(72) Inventors: Justin Coker, Laguna Niguel, CA (US); Steve S. Khalaj, Laguna Hills, CA (US); Paul D. Jun, La Crescenta, CA (US)

(73) Assignee: Avent, Inc., Alpharetta, GA (US)

( * ) Notice: Subject to any disclaimer, the term of this patent is extended or adjusted under 35 U.S.C. 154(b) by 404 days.

(21) Appl. No.: 16/308,980

(22) PCT Filed: Jun. 23, 2016

(86) PCT No.: PCT/US2016/038926
§ 371 (c)(1),
(2) Date: Dec. 11, 2018

(87) PCT Pub. No.: WO2017/222523
PCT Pub. Date: Dec. 28, 2017

(65) Prior Publication Data
US 2019/0175872 A1 Jun. 13, 2019

(51) Int. Cl.
*A61M 25/01* (2006.01)
*A61N 1/36* (2006.01)
(Continued)

(52) U.S. Cl.
CPC ......... *A61M 25/0108* (2013.01); *A61B 8/481* (2013.01); *A61N 1/36017* (2013.01);
(Continued)

(58) Field of Classification Search
CPC ................ A61B 8/481; A61B 17/3401; A61B 2017/3413; A61B 2090/3925;
(Continued)

(56) References Cited

U.S. PATENT DOCUMENTS 5,054,501 A 10/1991 Chuttani et al.
5,081,997 A 1/1992 Bosley, Jr. et al.
(Continued)

FOREIGN PATENT DOCUMENTS

EP 1 486 221 A 12/2004
EP 2 540 336 A1 1/2013
(Continued)

OTHER PUBLICATIONS

International Search Report and Written Opinion for PCT/US2016/038926, dated Feb. 23, 2017, 15 pages.
(Continued)

*Primary Examiner* — Amelie R Davis
(74) *Attorney, Agent, or Firm* — Dority & Manning, P.A.

(57) ABSTRACT

The present invention is directed to an echogenic catheter assembly. The catheter assembly includes a catheter having a proximal end and a distal end that defines a lumen extending from the proximal end to the distal end. Further, the catheter assembly includes a coil member configured with at least a portion of the lumen of the catheter. The coil member forms a plurality of outwardly extending projections. One or more of the outwardly extending projections define a cross-sectional shape having at least one non-arcuate edge. As such, the non-arcuate edges of the outwardly extending projections are configured to enhance ultrasonic imaging of the catheter when inserted into a patient.

14 Claims, 9 Drawing Sheets

(51) Int. Cl.
*A61B 8/08* (2006.01)
*A61N 1/04* (2006.01)
*A61M 25/00* (2006.01)
*A61F 7/00* (2006.01)
*A61B 90/00* (2016.01)
*A61B 8/12* (2006.01)
*A61M 25/09* (2006.01)

(52) U.S. Cl.
CPC .......... *A61B 8/12* (2013.01); *A61B 2090/3925* (2016.02); *A61F 7/007* (2013.01); *A61M 25/005* (2013.01); *A61M 25/09* (2013.01); *A61M 2205/36* (2013.01); *A61N 1/0456* (2013.01)

(58) Field of Classification Search
CPC .......... A61B 2090/3929; A61B 8/0841; A61B 90/39; A61M 25/005; A61M 25/0108; A61M 19/00; A61M 5/3286; A61M 5/3291
See application file for complete search history.

(56) References Cited

U.S. PATENT DOCUMENTS

| | | |
|---|---|---|
| 9,254,146 B2 | 2/2016 | Massengale et al. |
| 9,400,546 B1 | 7/2016 | Agarwal et al. |
| 2003/0191453 A1* | 10/2003 | Velez ................ A61M 25/0068 604/537 |
| 2004/0249288 A1 | 12/2004 | Ichikawa |
| 2005/0273076 A1* | 12/2005 | Beasley .............. A61M 25/007 604/526 |
| 2008/0051694 A1 | 2/2008 | Kato |
| 2012/0059308 A1* | 3/2012 | Hsu ...................... A61N 1/0502 604/21 |
| 2012/0095404 A1 | 4/2012 | Massengale et al. |
| 2015/0320979 A1* | 11/2015 | Fearnot ................. A61B 8/445 600/458 |

FOREIGN PATENT DOCUMENTS

| | | |
|---|---|---|
| JP | S 6446473 A | 2/1989 |
| JP | 202204832 A | 7/2002 |
| JP | 2006247148 A | 9/2006 |
| WO | WO 91/17698 A1 | 11/1991 |
| WO | WO 2005/120623 A2 | 12/2005 |
| WO | WO 2016/204759 A2 | 12/2016 |
| WO | WO 2016/204832 A1 | 12/2016 |

OTHER PUBLICATIONS

International Search Report and Written Opinion for PCT/US 2016/038926, dated Feb. 23, 2017, 15 pages.

* cited by examiner

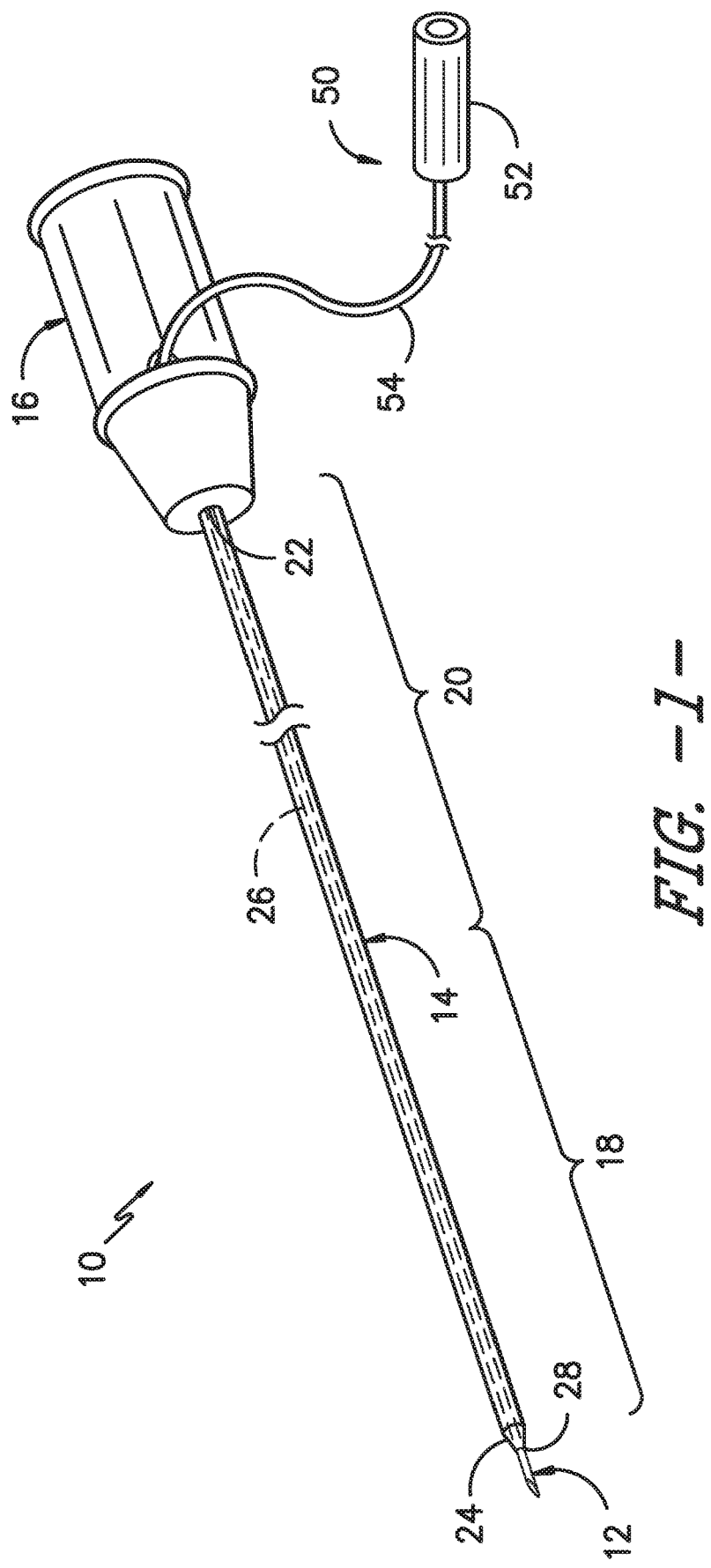
FIG. -1-

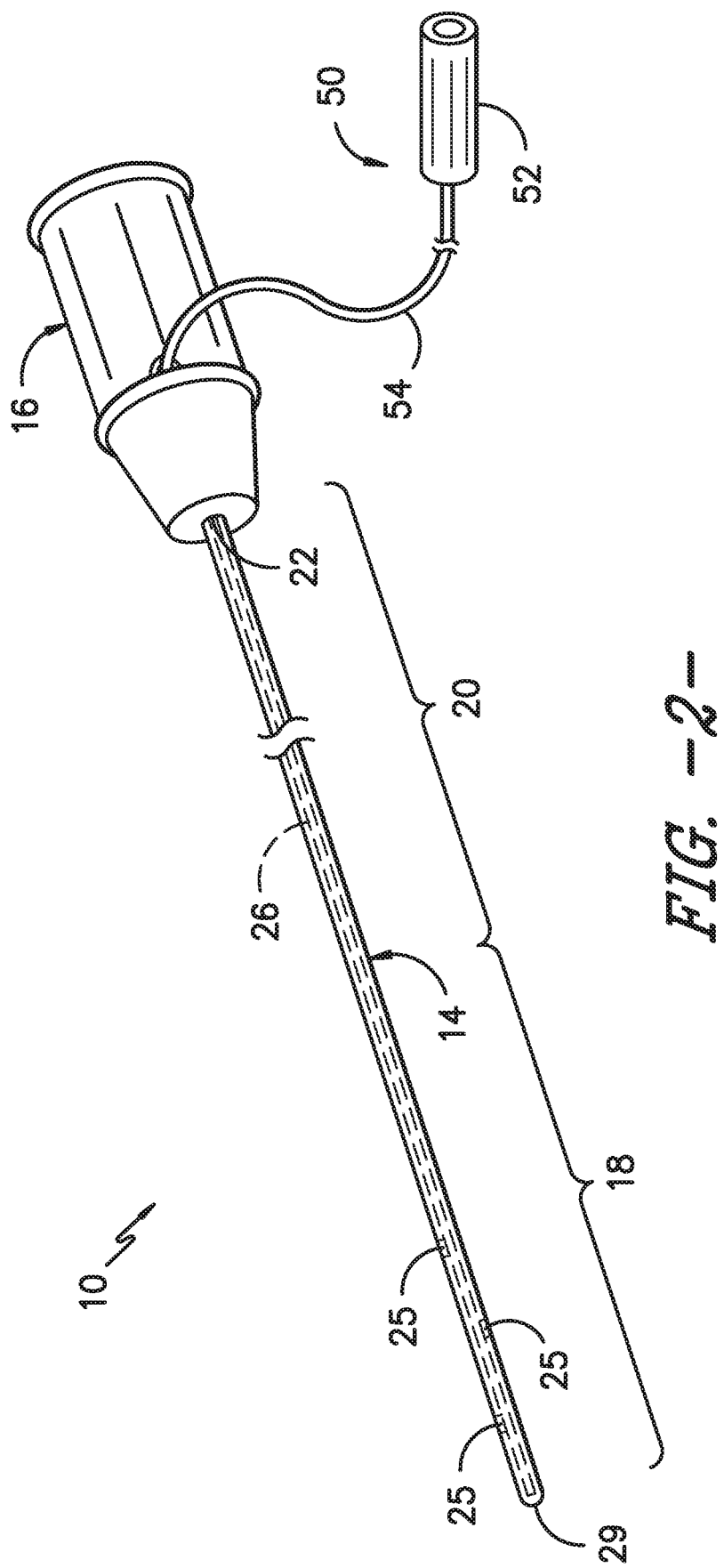
FIG. -2-

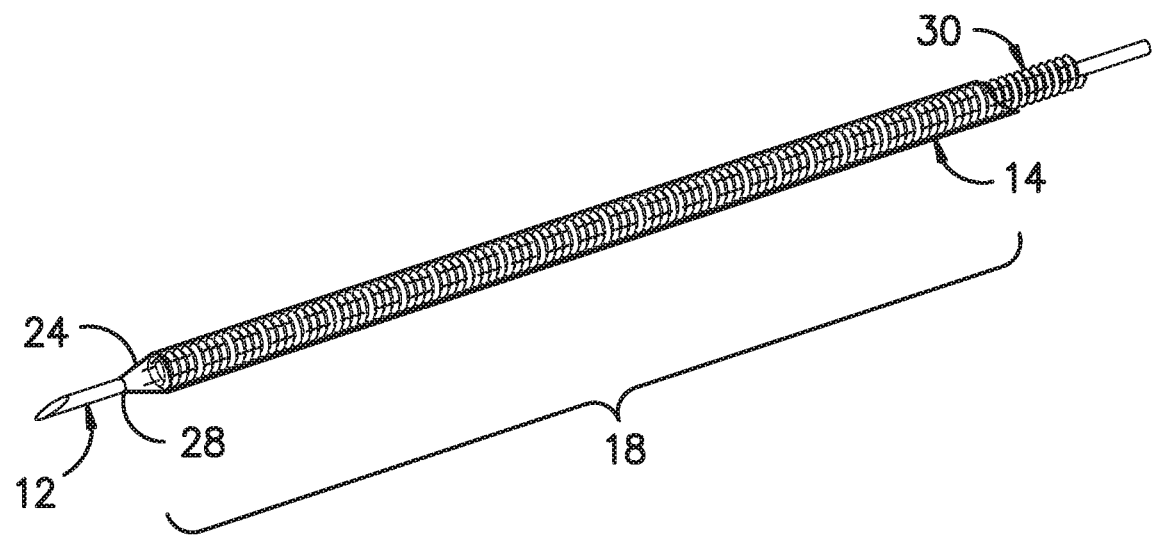
FIG. -3-
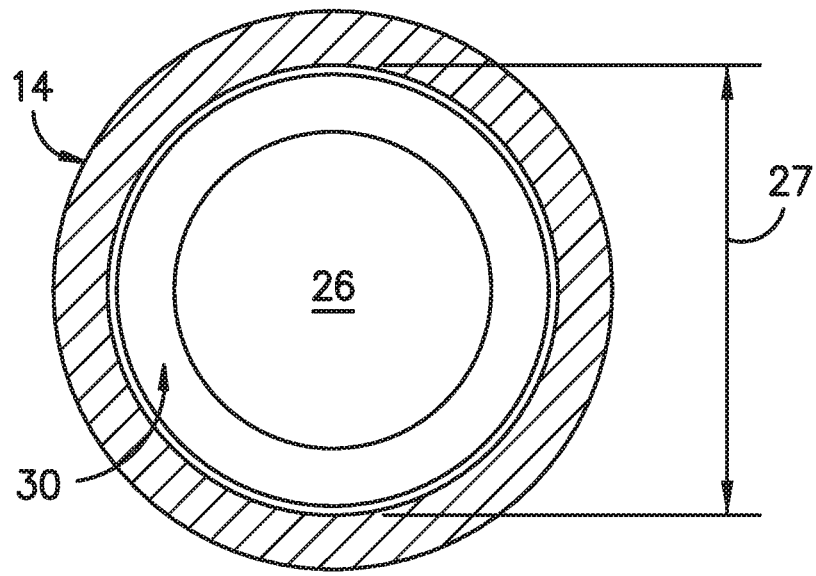
FIG. -4-

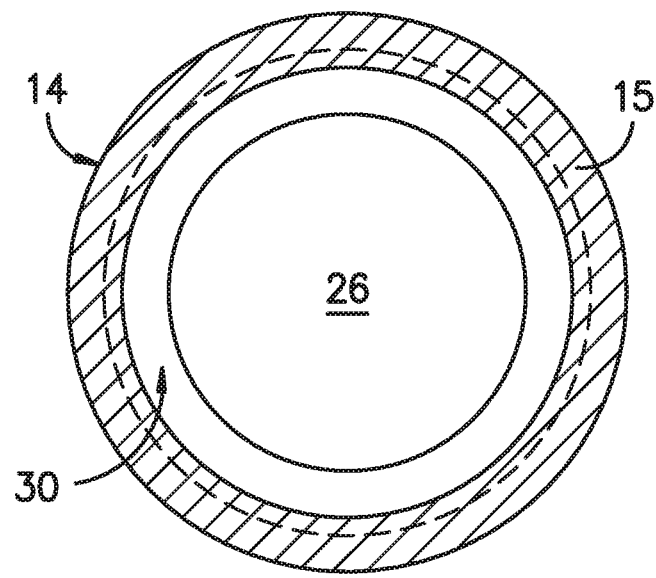
FIG. -5-
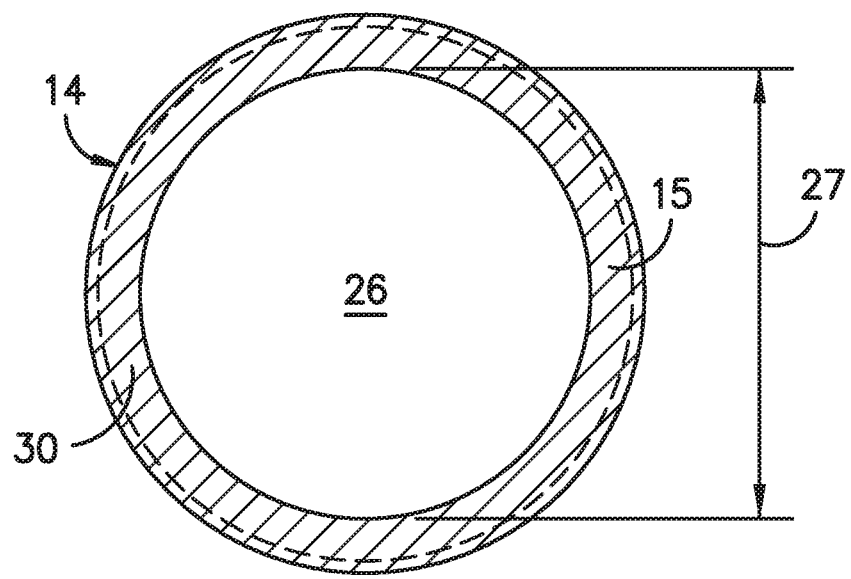
FIG. -6-

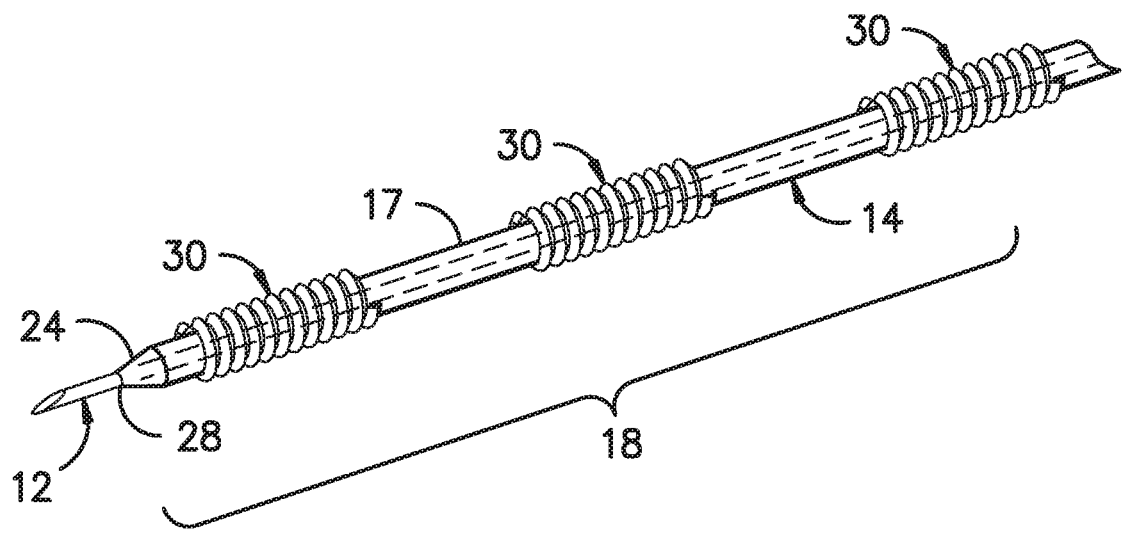
FIG. -7-
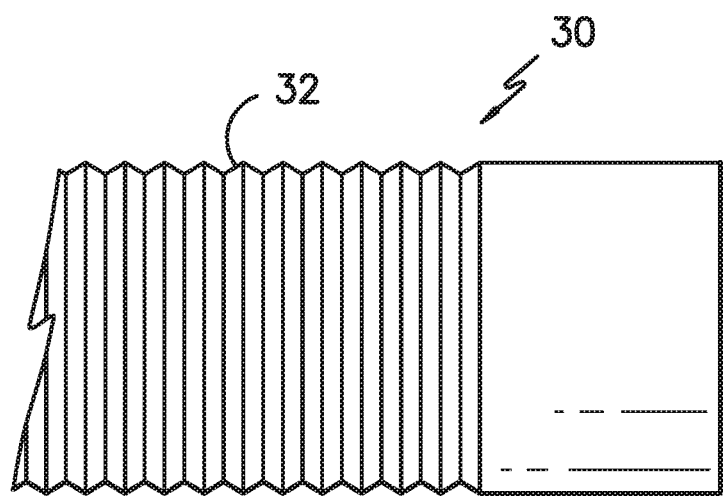
FIG. -8-

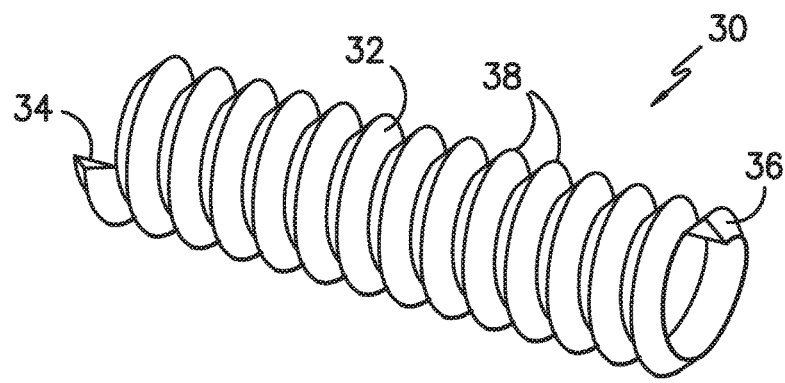
FIG. -9-
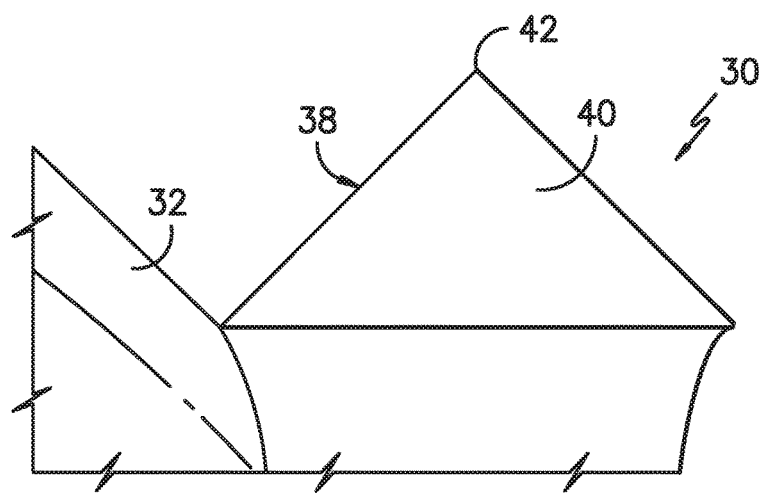
FIG. -10-

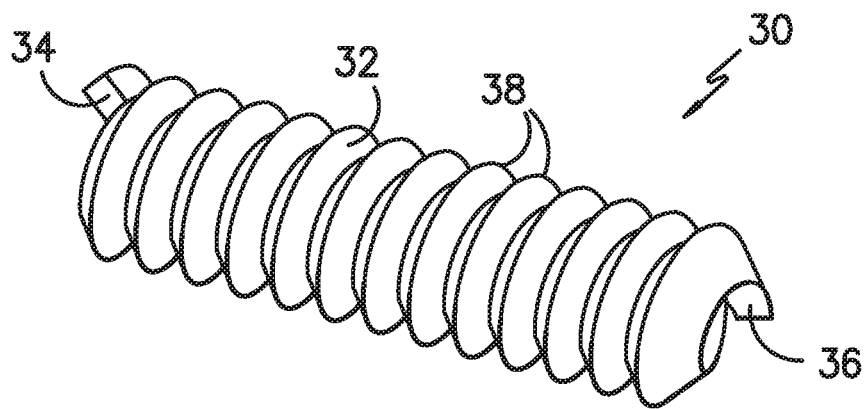
FIG. -11-
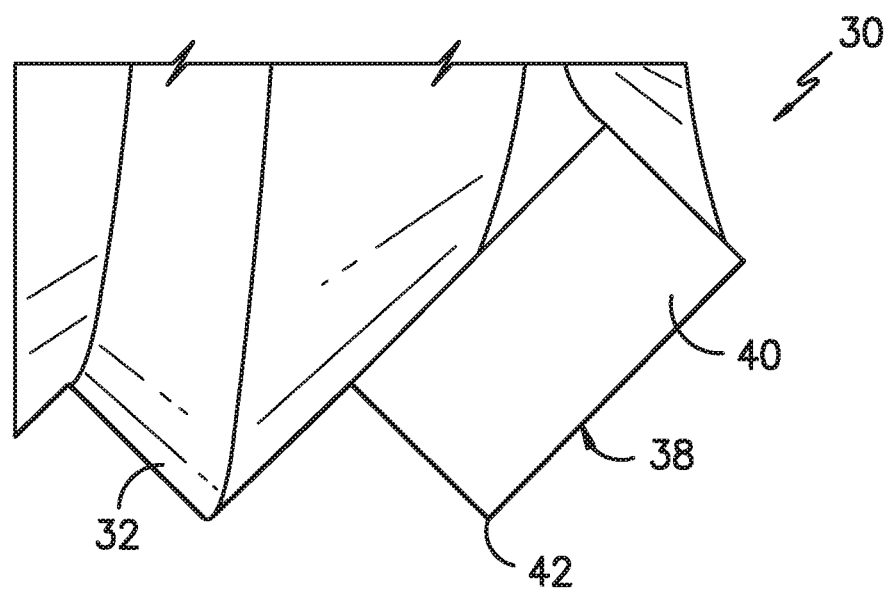
FIG. -12-

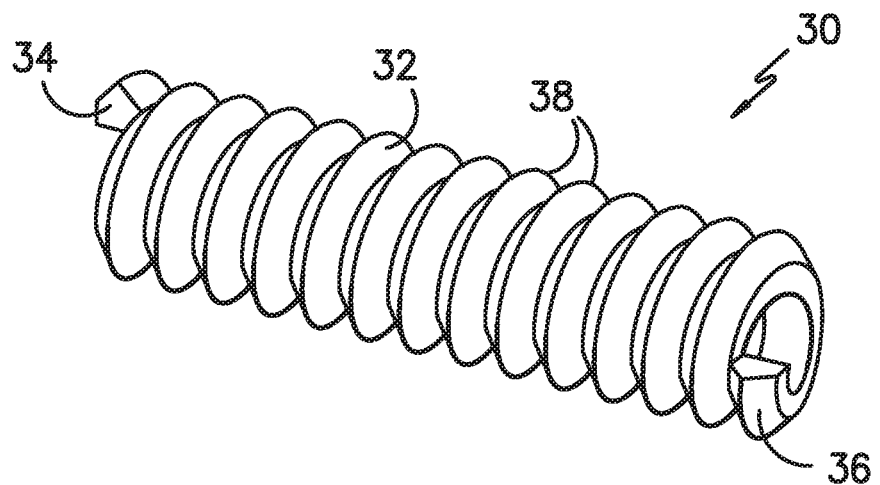
FIG. -13-
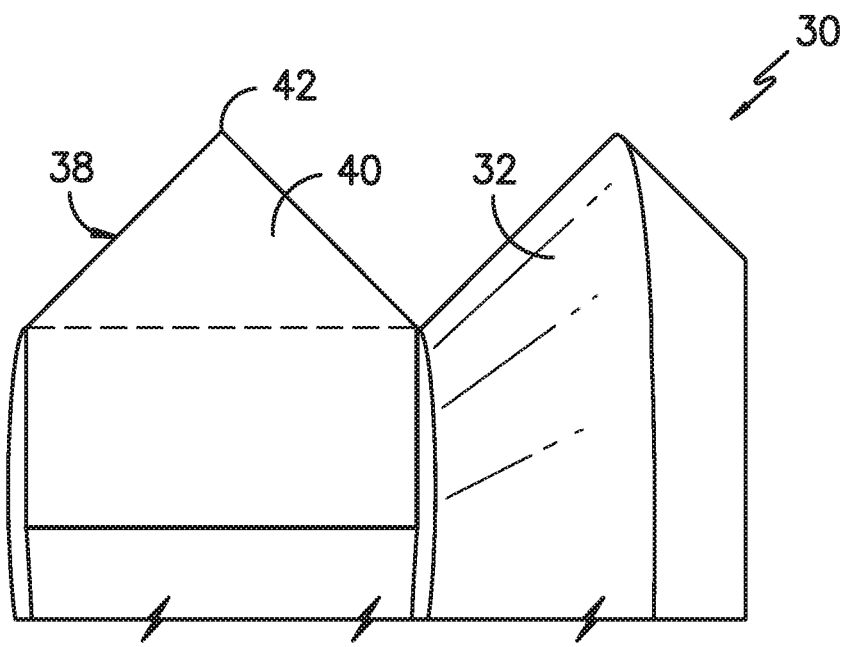
FIG. -14-

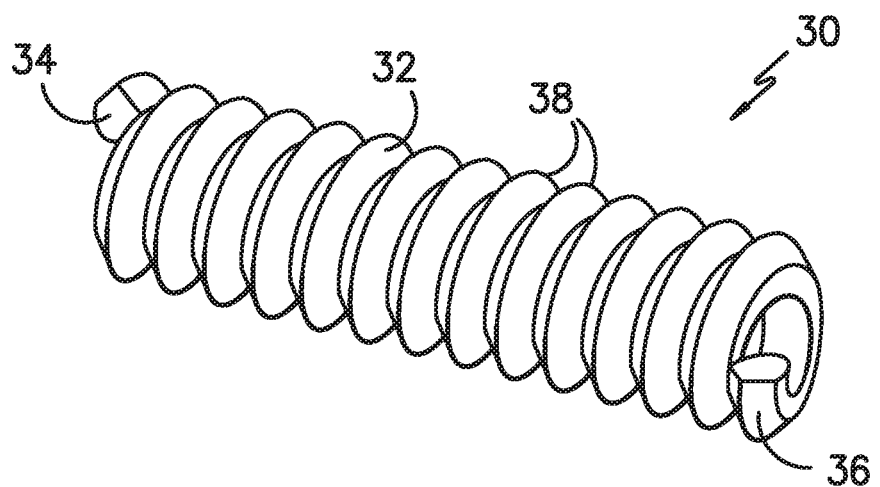
FIG. -15-
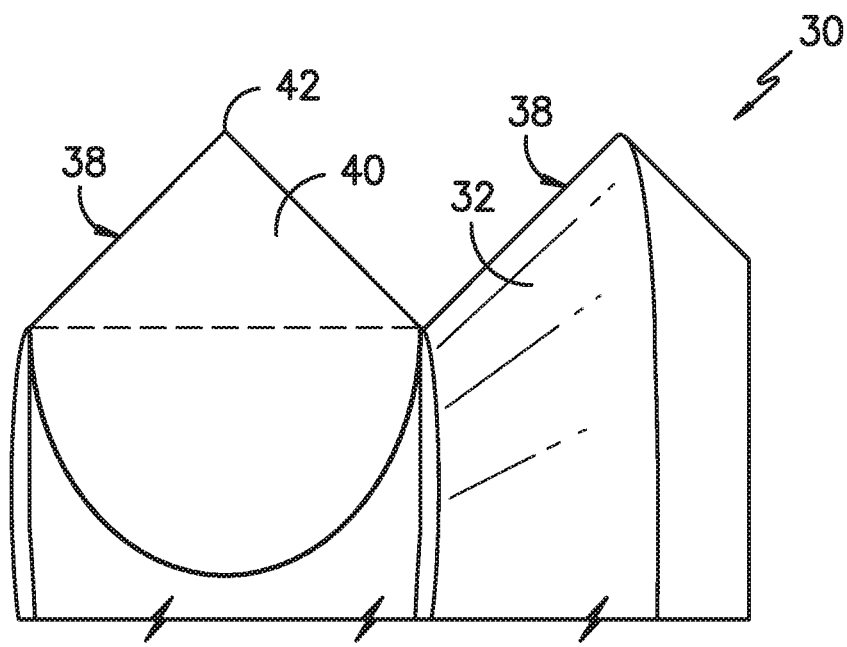
FIG. -16-

ECHOGENIC COIL MEMBER FOR A CATHETER ASSEMBLY

RELATED APPLICATION

This application is a national phase of and claims priority to PCT/US2016/038926, filed Jun. 23, 2016, the contents of which are incorporated herein by reference in its entirety hereto.

FIELD OF THE INVENTION

The present invention relates generally to echogenic devices and more particularly to an echogenic coil member for a catheter assembly that can be inserted into a medium, such as biological tissue, and viewed via ultrasound.

BACKGROUND

Ultrasonic imaging in the medical field is widely used for a variety of applications. In addition to imaging physiological structures and tissue such as organs, tumors, vessels, and the like, it is often desirable for a physician or technician to view an image of a medical device which has been inserted into the tissue or passageway of a patient. The types of devices which are surgically sterilized and inserted into patients are many. Typical examples include: needles, catheters, and a variety of other medical products such as stents, dilators, pacing leads, introducers, angiography devices, angioplasty devices, pacemakers, in-patient appliances such as pumps and other devices. For example, during a nerve block procedure, visibility of such medical devices under ultrasound is particularly important. More specifically, in such procedures, locating the catheter tip can be critical around the nerve sight. Various approaches have been used to enhance ultrasonic imaging of such devices by modifying the reflective surface characteristics of these devices.

U.S. Pat. No. 5,081,997 to Bosley, Jr. et al, entitled "Echogenic Devices, Material and Method," discloses a device such as a needle that includes an interface having a shape that is formed with a dimension that is less than a wavelength of the incident sonic beam. According to Bosley, Jr. et al., the shape includes a dimension such as a radius of curvature which is much less than the wavelength of the sonic beam. The interface may include the outside surface a device or article or material. That surface has a plurality of partially spherical discontinuities for producing a scattered component of the image in response to the incident beam. This image is produced regardless of the incident beam angle of which conventional devices depend for producing a reflected or constructive interference image. The scattered component of the image is produced when the radius of the partially spherical discontinuities or a dimension of another geometric shape or surface are much less than the wavelength of the incoming sonic beam.

U.S. Patent Application Publication No. 2004/0249288 to Ichikawa, entitled "Ultrasonic Puncture Needle" discloses a device including an array of doughnut shaped recesses having a center portion remaining as a protrusion. According to U.S. Publication No. 2004/0249288 A1, the recesses are also formed with faces, bottoms and sides being generally flat so to obtain reflection echoes with a great intensity for the incident ultrasonic waves with a shallow incident angle.

While the approaches described in U.S. Pat. No. 5,081,997 and U.S. Patent Application Publication No. 2004/0249288 have shown promise, further improvements have been sought that would result in a catheter assembly that provides enhanced ultrasonic imaging, in a manner that is inexpensive to manufacture, simple and reliable to use, and flexible.

Accordingly, the present disclosure is directed to a flexible echogenic coil member for a catheter assembly that provides enhanced ultrasonic imaging.

SUMMARY OF THE INVENTION

Objects and advantages of the invention will be set forth in part in the following description, or may be obvious from the description, or may be learned through practice of the invention.

In one aspect, the present invention is directed to an echogenic catheter assembly. The catheter assembly includes a catheter having a proximal end and a distal end that defines a lumen extending from the proximal end to the distal end. Further, the catheter assembly includes a coil member configured with at least a portion of the lumen of the catheter. Moreover, the coil member forms a plurality of outwardly extending projections. One or more of the outwardly extending projections define a cross-sectional shape having at least one non-arcuate edge. As such, the non-arcuate edges of the outwardly extending projections are configured to enhance ultrasonic imaging of the catheter when inserted into a patient.

In one embodiment, the coil member may be located or positioned at the distal end of the catheter. In alternative embodiments, the coil member may extend entirely from the proximal end of the catheter to the distal end of the catheter. In yet another embodiment, the catheter assembly may include a plurality of coil members spaced apart or adjacent one another along a length of the catheter so as to increase or maintain flexibility of the catheter.

More specifically, in particular embodiments, the cross-sectional shapes of the outwardly extending projections may include any one of or combination of the following shapes: a rectangular, a triangle, a square, or similar.

In further embodiments, the coil member(s) may fit at least partially around an outer surface of the catheter. In alternative embodiments, the coil member(s) may be at least partially embedded into an interior wall of the catheter. More specifically, in certain embodiments, the coil member(s) may be embedded into the interior wall of the catheter so as to not change an inner diameter of the lumen of the catheter. In yet another embodiment, the coil member(s) may simply fit within the lumen of the catheter rather than being embedded therein.

In certain embodiments, the coil member may be a guide wire. In such embodiments, the guide wire may be coiled along its entire length or may be coiled only along a portion of its length such that the remaining portion is a solid wire.

In additional embodiments, the coil member(s) may be constructed of any suitable material, such as a metal or metal alloy. More specifically, in certain embodiments, the metals or metal alloys may include at least one of or a combination of the following: aluminum, titanium, copper, tin, nickel, zinc, magnesium, stainless steel, or any similar.

In yet another embodiment, the catheter assembly may be an over-the-needle catheter assembly having an open distal tip. In such embodiments, the needle may extend through the lumen and the open distal tip of the catheter.

In alternative embodiments, the catheter may have a closed distal tip with one or more infusion holes configured in an outer surface thereof. As such, the infusion holes are configured to allow a medication flowing through the lumen of the catheter to exit therethrough.

In another aspect, the present disclosure is directed to an echogenic coil member for a catheter assembly. The coil member includes a body configured for arrangement with at least a portion of a lumen of a catheter of the catheter assembly. Further, the body forms a plurality of outwardly extending projections. Moreover, one or more of the outwardly extending projections define a cross-sectional shape having at least one non-arcuate edge. As such, the non-arcuate edges of the outwardly extending projections are configured to enhance ultrasonic imaging of the catheter when inserted into a patient. It should also be understood that the coil member may be further configured according to the any of the embodiments as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an echogenic catheter assembly according to the present disclosure;

FIG. 2 illustrates a perspective view of another embodiment of an echogenic catheter assembly according to the present disclosure;

FIG. 3 illustrates a detailed perspective view of one embodiment of an echogenic catheter assembly according to the present disclosure, particularly illustrating a coil member configured within a lumen of a catheter of the catheter assembly;

FIG. 4 illustrates a cross-sectional view of one embodiment of an echogenic catheter assembly according to the present disclosure, particularly illustrating a coil member that fits within a lumen of a catheter of the catheter assembly;

FIG. 5 illustrates a cross-sectional view of one embodiment of an echogenic catheter assembly according to the present disclosure, particularly illustrating a coil member partially embedded within a lumen of a catheter of the catheter assembly;

FIG. 6 illustrates a cross-sectional view of one embodiment of an echogenic catheter assembly according to the present disclosure, particularly illustrating a coil member completely embedded within a lumen of a catheter of the catheter assembly;

FIG. 7 illustrates a detailed perspective view of one embodiment of an echogenic catheter assembly according to the present disclosure, particularly illustrating a plurality of coil members configured with an outer surface of a catheter of the catheter assembly;

FIG. 8 illustrates a partial, side view of one embodiment of a coil member for an echogenic catheter assembly according to the present disclosure, particularly illustrating an echogenic profile of the coil member;

FIG. 9 illustrates a perspective view of one embodiment of a coil member for an echogenic catheter assembly according to the present disclosure, particularly illustrating the outwardly extending projections of the coil member having a triangular cross-sectional shape;

FIG. 10 illustrates a cross-sectional view of one of the outwardly extending projections of the coil member of FIG. 9;

FIG. 11 illustrates a perspective view of one embodiment of a coil member for an echogenic catheter assembly according to the present disclosure, particularly illustrating the outwardly extending projections of the coil member having a rectangular cross-sectional shape;

FIG. 12 illustrates a cross-sectional view of one of the outwardly extending projections of the coil member of FIG. 11;

FIG. 13 illustrates a perspective view of one embodiment of a coil member for an echogenic catheter assembly according to the present disclosure, particularly illustrating the outwardly extending projections of the coil member having a house-shaped cross-sectional shape;

FIG. 14 illustrates a cross-sectional view of one of the outwardly extending projections of the coil member of FIG. 13;

FIG. 15 illustrates a perspective view of one embodiment of a coil member for an echogenic catheter assembly according to the present disclosure, particularly illustrating the outwardly extending projections of the coil member having a pie-shaped cross-sectional shape; and FIG. 16 illustrates a cross-sectional view of one of the outwardly extending projections of the coil member of FIG. 15.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site and/or the patient (e.g., the distal end of the catheter is the end oriented towards a catheter insertion site of the patient), and "proximal" refers to the opposite direction (e.g., the proximal end of the catheter is inserted into the distal end of a fluid delivery device).

Generally, the present disclosure is directed to an echogenic coil member for a catheter assembly. The catheter assembly includes a catheter having a proximal end and a distal end that defines a lumen extending from the proximal end to the distal end. As such, the coil member may be configured with at least a portion of the lumen of the catheter. Further, the coil member forms a plurality of outwardly extending projections with each projection defining a cross-sectional shape having at least one non-arcuate edge. As such, the non-arcuate edges of the outwardly extending projections are configured to enhance ultrasonic imaging of the catheter when inserted into a patient.

As used herein, the coil member of the present disclosure may include any suitable coil now known or later developed for the healthcare industry, such as coils configured as guide wires, coil-reinforced tubing or catheters, or similar. Further, it should be understood that the coil members of the present disclosure may be coiled along their entire length or coiled only along a portion of their length such that the remaining portion is a solid wire.

Referring now to the drawings, FIGS. 1 and 2 illustrate various embodiments of an echogenic catheter assembly 10 according to the present disclosure. For example, as shown, the catheter assembly 10 includes a catheter 14 having a proximal end 22 and a distal end 24. More specifically, as shown in FIG. 1, the catheter assembly 10 may be an over-the-needle (OTN) catheter assembly, i.e. the catheter 14 is coaxially mounted to the needle 12. Thus, the catheter assembly 10 may be configured such that the catheter 14 and needle 12 can be simultaneously inserted into a patient. Alternatively, as shown in FIG. 2, the catheter 14 may be used without a needle 12. In addition, the catheter 14 (and/or the needle 12) defines a lumen 26 extending from the proximal end 22 to the distal end 24 of the catheter 14. Thus, the catheter 14 is configured to deliver a treatment fluid to a targeted site, e.g. a nerve bundle, within the patient via the lumen 26. More specifically, as shown in FIG. 1, the catheter assembly 10 may include an open distal tip 28 such that the needle 12 may extend beyond the open distal tip 28.

In alternative embodiments, as shown in FIG. 2, the catheter assembly 10 may include a closed distal tip 29, e.g. depending on the desired delivery application of the treatment fluid to the patient. More specifically, as shown, the catheter assembly 10 may include a closed distal tip 29 without the needle 12. In such an embodiment, the catheter 14 may contain one or more infusion holes 25 configured on an outer surface 17 thereof so as to deliver a treatment fluid to a targeted site within a patient via the lumen 26 of the catheter 14. In addition, it should also be understood that the catheter assemblies according to the present disclosure may optionally include one or more infusion holes as well as the open distal tip 28 for administering a treatment fluid to a patient.

More specifically, in certain embodiments, the proximal end 22 of the catheter 14 may include a hub 16 configured thereon for mating communication with a fluid delivery device (not shown) such that a treatment fluid can be delivered to a targeted site within a patient via the lumen 26 and the open distal tip 28 and/or the infusion holes 25 of the catheter 14 and/or needle 12. The fluid delivery device as described herein may be any suitable device known in the art, such as a pump, reservoir, syringe, or the like. Further, the hub 16 may have any conventional configuration, such as a Luer-lock fitting.

Still referring to FIGS. 1 and 2, the echogenic catheter assembly 10 may also include a heat application assembly 50 configured to apply heat to the catheter 14 (or the needle 12 where applicable) or any other suitable component of the catheter assembly 10, such as the coil member 30 as described herein. For example, as shown, the heat application assembly 50 may be coupled with the hub 16 of the catheter 14 so as to apply heat or current to the catheter assembly 10. In additional embodiments, the nerve stimulator apparatus 50 may be configured to apply current through the coil member 30 for use during various medical procedures. Further, the heat application assembly 50 may correspond to a nerve stimulator apparatus having a nerve stimulator 52 that provides heat or current through one or more stimulator wires 54. It should be understood, however, that the heat application assembly 50 can further include any other suitable heating assembly known in the art and the illustrated embodiment is provided for illustrative purposes only. For example, in further embodiments, the heat application assembly 50 may also include one or more battery devices, temperature-controlled water, an ultrasound device, a vibration device, or similar.

Referring now to FIGS. 3-16, the echogenic catheter assembly 10 also includes one or more echogenic coil members 30 configured to enhance ultrasonic imaging of the catheter assembly 10. More specifically, as shown in FIGS. 3-7, the coil member 30 may be configured with at least a portion of the lumen 26 of the catheter 14. As such, the coil member 30 is configured to provide support to the catheter 14 as the catheter 14 is inserted within a patient and/or during a medical procedure while also remaining flexible.

For example, as shown in FIG. 4, the coil member(s) 30 may be sized to fit within an inner diameter 27 of the lumen 26 of the catheter 14, e.g. such that the coil member(s) 30 can be easily inserted therethrough. Alternatively, as shown in FIGS. 5 and 6, the coil member(s) 30 may be embedded into at least a portion of an interior wall 15 of the catheter 14. For example, in certain embodiments, as shown in FIG. 5, the coil member(s) 30 may be partially embedded into the interior wall 15 of the catheter 14. Alternatively, as shown in FIG. 6, the coil member 30(s) may be completely embedded within the interior wall 15 of the lumen 26 of the catheter 14 such that the internal diameter 27 of the lumen 26 catheter 14 remains unchanged and the needle 12 (if present) can easily fit therethrough. In yet another embodiment, as shown in FIG. 7, the coil member(s) 30 may fit at least partially around an outer surface 17 of the catheter 14.

In additional embodiments, as generally shown in FIGS. 3 and 7, the coil member(s) 30 may be located within the distal region 18, such as at the distal end 24, of the catheter 14. In alternative embodiments, the coil member(s) 30 may also be located within the proximal region 20, such as at the proximal end 22, of the catheter 14. In yet another embodiment, as shown in FIG. 3, the coil member(s) 30 may extend entirely from the proximal end 22 of the catheter 14 to the distal end 24 of the catheter 14. Further, as shown in FIG. 7, the catheter assembly 10 may include a plurality of coil members 30 spaced apart along a length of the catheter 14 either within the lumen 26 or outside of the lumen 26 as described herein.

More specifically, as shown particularly in FIGS. 7-9, 11, and 13, the coil member(s) 30 defines an outer surface 32 that extends from a proximal end 34 to a distal end 36. Further, as shown generally in FIGS. 3-14, the coil member(s) 30 is coiled to form a plurality of outwardly extending projections 38. In addition, as generally shown, one or more of the outwardly extending projections 38 define a cross-sectional shape 40 having at least one non-arcuate edge 42. As such, the non-arcuate edges 42 of the outwardly extending projections 38 of the coil member(s) 30 are configured to enhance ultrasonic imaging of the catheter 14 when inserted into a patient.

The cross-sectional shapes 40 of the outwardly extending projections 38 of the coil member(s) 30 as described herein may include any suitable cross-sectional shape that forms at least one non-arcuate edge 42. For example, in particular embodiments, the cross-sectional shapes 40 of the outwardly extending projections 38 of the coil member(s) 30 may include any one of or combination of the following shapes: a rectangular, a triangle, a square, or similar. More specifically, as shown in FIGS. 9 and 10, the cross-sectional shape 40 of the outwardly extending projections 38 of the coil member(s) 30 may include a triangle. Alternatively, as shown in FIGS. 11 and 12, the cross-sectional shape 40 of the outwardly extending projections 38 of the coil member (s) 30 may include a rectangle. In yet another embodiment, the cross-sectional shape 40 of the outwardly extending projections 38 of the coil member(s) 30 may include a combination of shapes. For example, as shown in FIGS. 13 and 14, the cross-sectional shape 40 of the outwardly extending projections 38 of the coil member(s) 30 may include both a triangle and a rectangle so as to form a house-shaped cross-sectional shape. In additional embodiments, as shown in FIGS. 15 and 16, the cross-sectional shape 40 of the outwardly extending projections 38 may include both a triangle and an arcuate shape, such as a semicircle, so as to form an overall pie-shaped cross-sectional shape. As such, it should be understood that any suitable shapes or combination of shapes may be utilized so as to form the outwardly extending projections 38 having at least non-arcuate edge 42 of that enhance ultrasonic imaging of the catheter 14.

In additional embodiments, the coil member 30 may be constructed of any suitable echogenic material. For example, in specific embodiments, the echogenic coil member 30 may be constructed of a metal or a metal alloy. More particularly, the metal or metal alloy may include at least one of or a combination of the following: aluminum, titanium, copper, tin, nickel, zinc, magnesium, stainless steel, or similar.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An echogenic catheter assembly, comprising:
   a catheter comprising a proximal end and a distal end and defining a lumen extending from the proximal end to the distal end; and
   a coil member arranged with at least a portion of the lumen of the catheter, the coil member forming a plurality of outwardly extending projections, each of the plurality of outwardly extending projections defining a cross-sectional shape comprising a combination of a triangle having a non-arcuate edge and at least one of an ellipse or a quadrilateral, each of the non-arcuate edges defining a vertex at which two sides of one of the cross-sectional shapes intersect at an outermost point of one of the cross-sectional shapes, the non-arcuate edges of the plurality of outwardly extending projections configured to enhance ultrasonic imaging of the catheter when inserted into a patient.

2. The catheter assembly of claim 1, wherein the coil member is located at the distal end of the catheter.

3. The catheter assembly of claim 1, wherein the coil member extends from the proximal end of the catheter to the distal end of the catheter.

4. The catheter assembly of claim 1, wherein the coil member fits at least partially around an outer surface of the catheter.

5. The catheter assembly of claim 1, wherein the coil member is at least partially embedded into an interior wall of the catheter.

6. The catheter assembly of claim 5, wherein the coil member is embedded into the interior wall of the catheter so as to not change an inner diameter of the lumen of the catheter.

7. The catheter assembly of claim 1, wherein the coil member is a guide wire.

8. The catheter assembly of claim 1, wherein the coil member fits within the lumen of the catheter.

9. The catheter member of claim 1, wherein the coil member is constructed of a metal or metal alloy.

10. The catheter member of claim 9, wherein the metal or metal alloy comprises at least one of or a combination of the following: aluminum, titanium, copper, tin, nickel, zinc, magnesium, or stainless steel.

11. The catheter assembly of claim 1, wherein the catheter assembly comprises an over-the-needle catheter assembly comprising a needle, the catheter comprising an open distal tip with the needle extending through the lumen and the open distal tip of the catheter.

12. The catheter assembly of claim 1, wherein the catheter comprises a closed distal tip and one or more infusion holes configured in an outer surface thereof, the infusion holes configured to allow a medication flowing through the lumen of the catheter to exit therethrough.

13. An echogenic coil member assembly for a catheter, comprising:
    at least one coil member capable of being arranged within a lumen of the catheter, the coil member comprising a plurality of outwardly extending projections, each of the plurality of outwardly extending projections defining a cross-sectional shape comprising a combination of a triangle having a non-arcuate edge and at least one of an ellipse or a quadrilateral, each of the non-arcuate edges defining a vertex at which two sides of one of the cross-sectional shapes intersect at an outermost point of one of the cross-sectional shapes, the non-arcuate edges of the plurality of outwardly extending projections configured to enhance ultrasonic imaging of the catheter when inserted into a patient.

14. The echogenic coil member assembly of claim 13, wherein the coil member is constructed of a metal or metal alloy, wherein the metal or metal alloy comprises at least one of or a combination of the following: aluminum, titanium, copper, tin, nickel, zinc, magnesium, or stainless steel.

* * * * *